(12) United States Patent
Bombardelli et al.

(10) Patent No.: US 6,429,202 B1
(45) Date of Patent: Aug. 6, 2002

(54) PHOSPHOLIPID COMPLEXES OF PROANTHOCYANIDIN A2 AS ANTIATHEROSCLEROTIC AGENTS

(75) Inventors: Ezio Bombardelli; Paolo Morazzoni, both of Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 09/857,804

(22) PCT Filed: Dec. 13, 1999

(86) PCT No.: PCT/EP99/09854

§ 371 (c)(1),
(2), (4) Date: Jun. 11, 2001

(87) PCT Pub. No.: WO00/37062

PCT Pub. Date: Jun. 29, 2000

(30) Foreign Application Priority Data

Dec. 18, 1998 (IT) .......................................... MI98A2732

(51) Int. Cl.⁷ .......................... A61K 31/35; A61K 31/66
(52) U.S. Cl. ......................... 514/78; 514/100; 514/114; 514/119; 514/450; 514/452; 514/453; 514/456; 424/450; 424/456; 424/464; 549/220; 549/352

(58) Field of Search .......................... 514/78, 100, 114, 514/452, 119, 450, 453, 456; 424/450, 456, 464; 549/220, 352

(56) References Cited

U.S. PATENT DOCUMENTS

| 4,698,360 A | | 10/1987 | Masquelier | 514/456 |
| 4,863,956 A | * | 9/1989 | Gabetta et al. | 514/453 |
| 4,963,527 A | * | 10/1990 | Bombardelli et al. | 514/25 |
| 5,648,377 A | | 7/1997 | Bombardelli et al. | 514/456 |

FOREIGN PATENT DOCUMENTS

| EP | 1 210 785 | 2/1987 |
| EP | 0 713 706 | 5/1996 |
| WO | WO 99/29331 | 7/1999 |

* cited by examiner

*Primary Examiner*—Frederick Krass
(74) *Attorney, Agent, or Firm*—Pennie & Edmonds LLP

(57) ABSTRACT

The present invention relates to complexes of proanthocyanidin A2 and one or more phospholipids, pharmaceutical compositions containing the complex of proanthocyanidin A2 and one or more phospholipids, and methods of treating or preventing atherosclerosis and myocardial and cerebral infarction in a patient by administering the complex of proanthocyanidin A2 and one or more phospholipids, as well as methods of forming such complexes

16 Claims, No Drawings

PHOSPHOLIPID COMPLEXES OF PROANTHOCYANIDIN A2 AS ANTIATHEROSCLEROTIC AGENTS

This application is a 371 of PCT/EP99/09854, filed Dec. 13, 1999.

TECHNICAL FIELD

The present invention relates to phospholipid complexes of proanthocyanidin A2 or of extracts enriched in proanthocyanidin A2 and the use thereof for the preparation of medicaments for the prophylaxis and the therapy of atherosclerosis, and myocardial and cerebral infarction.

BACKGROUND OF THE INVENTION

Proanthocyanidin A2 or 8,14-methano-2H, 14H-1-benzopyrano[7,8-d] [1,3]benzodioxocin-3,5,11,13,15-pentol-2,8-bis-(3,4-dihydroxyphenyl)3,4-dihydroxyphenyl) 3,4-dihydro[2R-2α,3α,8β,14β,15R] of formula (I)

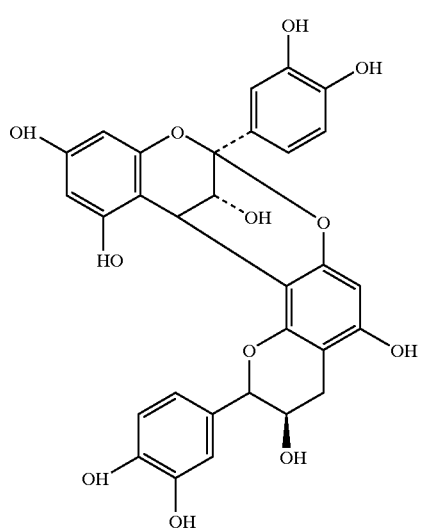

was isolated from seed of *Aesculus hippocastanum* (Tetrahedron Lett., 429, 1966). The therapeutical use of proanthocyanidin A2 as cicatrising, cytoprotective, antiulcer, venotonic, vasoprotective and antiperoxidative agent is disclosed in EP-A-210785 (Feb. 4, 1987).

SUMMARY OF THE INVENTION

It has now surprisingly been found that the phospholipid complexes of proanthocyanidin A2 exert a marked antiatherosclerotic activity both in animals and in humans when administered systemically, preferably through the oral route.

The complexes of the invention can consist of natural or synthetic phospholipids, such as lecithins, phosphatidylcholine, phosphatidylserine, phosphatidylethanolamine. The ratio of proanthocyanidin A2 to phospholipids ranges from 2:1 to 1:2, and preferably is about 1:1.5 w/w. A particularly preferred complex is that with soy phosphatidylcholine.

The complexes of the invention are prepared by reacting a solution of the phospholipid with a solution of proanchocyanidin A2 in suitable solvents, such as acetone, ethyl acetate, ethanol, then concentrating the reaction mixture under reduced pressure, to obtain a thick residue which can be ground.

The complexes of the invention dose-dependently prevent or reduce the formation of, atherosclerotic plaques. The activity was evidenced in rabbits fed with a hypercholesterolemic diet so as to induce atherosclerotic lesions similar to the human ones at the vasal level, particularly at the aortal arch, ventral aorta, carotids and cerebral vessels. In said model, the above mentioned phospholipid complexes change the macro- and microscopical vascular condition reducing, compared with untreated animals, both the number and the severity of the atheromatous plagues, with surprising vascular-tissutal benefit. In another atherosclerosis model, with the purpose of cerebral protection, wherein the vasal lumen of rabbit internal carotid had been surgically reduced while administering a hypercholesterolemic diet rich in saturated fats, a decrease in carotid obstruction, a reduction of vasal walls thickness and increased survival of the animals were observed. Atherosclerotic patients showed, after six month-treatment, a reduction of carotid obstruction due to atheromatous plaques and an improved carotid flow, evaluated by Doppler ultrasonography.

The phospholipid complexes of proanthocyanidin A2 can be used in suitable administration forms for the oral route such as tablets, soft- or hard-gelatin capsules, at dosages ranging from 50 to 500 mg two-three times a day, depending on the severity of the disease. The preparation of the pharmaceutical formulations can be carried out according to conventional techniques and excipients.

DETAILED DESCRIPTION OF THE PREFERRED EMBODIMENTS

The following examples illustrate the invention in greater detail.

EXAMPLE 1

Preparation of the Complex of Proanthocyanidin A2 with Phosphatidylcholine

A solution of 1577 g of phosphatidylcholine in 5 liters of ethyl acetate, kept at 70° C., was added with a solution of 1 kg of proanthocyanidin A2 in 5 liters of acetone.

The mixture was refluxed under stirring and evaporated to dryness under vacuum. The residue was dried under vacuum at 50° C. for 24 h, then ground to the desired particle size.

EXAMPLE 2

32 New Zealand rabbits were divided in 4 groups of 8 animals each, and treated as follows:

Group 1): Control, normal diet
Group 2): Hypercholesterolemic diet (0.2% w/w cholesterol)
Group 3): Hypercholesterolemic diet+phospholipid complex of proanthocyanidin A2 extract (0.2% cholesterol+ 2% w/w complex of Example 1).
Group 4): Hypercholesterolemic diet+proanthocyanidin A2 extract (0.2% cholesterol+amount of proanthocyanidin A2 equivalent to that present in 2% w/w of the complex of Example 1). After 8 week-treatment, during which cholesterol, LDL/VLDL, HDL and triglycerids levels were measured, the animals were killed.

The number, size and distribution of the atherosclerotic lesions on thoracic and abdominal aorta were evaluated.

Aorta strips were fixed and stained with Sudan IV to visualize the lesions and to evaluate the vasal cholesterol and the content in oxidized cholesterol by gaschromatography.

The results reported in the following table prove that the treatment with phospholipid complexes of Proanthocyanidin A2 decreases in a statistically significant way the atherosclerotic lesions induced by hypercholesterolemic diet.

TABLE

| Treatment | area percent of the lesion |
|---|---|
| Group 1 | 0.5% |
| Group 2 | 34% |
| Group 3 | 7.5%* |
| Group 4 | 30% |

*p < 0.01 compared with group 2.

EXAMPLE 3

Capsules Containing 500 mg of Phospholipid Complex of Proanthocyanidin A2
Composition:

| | |
|---|---|
| Complex of Proanthocyanidin A2 with soy phosphatidylcholine | 150 mg |
| Lactose | 57 mg |
| Modified starch | 40 mg |
| Magnesium stearate | 3.0 mg |

EXAMPLE 4

| Gastro-resistant tablets | |
|---|---|
| Complex of Proanthocyanidin A2 with soy phosphatidylcholine | 200 mg |
| Microcrystalline cellulose | 118 mg |
| Precipitated silica | 3 mg |
| Magnesium stearate | 4 mg |
| Methacrylic acid anionic polymer and esters thereof | 12 mg |
| Talc | 8 mg |
| Magnesium carbonate | 8 mg |
| Maize starch | 5 mg |
| Gum arabic | 159 mg |

EXAMPLE 5

| Soft-gelatin capsules | |
|---|---|
| Complex of Proanthocyanidin A2 with soy phosphatidylcholine | 216 mg |
| Peanut oil | 209 mg |
| Partially hydrogenated vegetable oils | 100 mg |
| Soy lecithin | 5 mg |

What is claimed is:

1. A composition comprising a complex of proanthocyanidin A2 and one or more phospholipids.

2. The composition of claim 1, wherein the phospholipid is selected from the group consisting of lecithins, phosphatidylcholine, phosphatidylethanolamine, phosphatidylserine, and mixtures thereof.

3. The composition of claim 2, wherein the phospholipid is soy phosphatidylcholine.

4. The composition of claim 1, wherein the ratio of the proanthocyanidin A2 to phospholipid is from 2:1 to 1:2 w/w.

5. A pharmaceutical composition comprising a complex of proanthocyanidin A2 and one or more phospholipids and one or more pharmaceutically acceptable excipients.

6. The pharmaceutical composition of claim 5, wherein the amount of the complex is from 50 to 500 mg.

7. The pharmaceutical composition of claim 5 in the form of a tablet, soft-gelatin capsule, or hard-gelatin capsule.

8. A method of treating or preventing atherosclerosis, or myocardial or cerebral infarction in a mammal comprising administering to the mammal a therapeutically effective amount of a complex of a&proanthocyanidin A2 and one or more phospholipids.

9. The method of claim 8, wherein the complex is administered orally.

10. The method of claim 9, wherein the complex is administered between 2 and 3 times a day in an amount of 50 to 500 mg per administration.

11. A method of forming a complex of proanthocyanidin A2 and one or more phospholipids comprising:

reacting the one or more phospholipids with proanthocyanidin A2 in a solution; and concentrating the solution to provide a crude complex of proanthocyanidin A2 and one or more phospholipids.

12. The method of claim 11, further comprising refluxing the solution.

13. The method of claim 11, further comprising drying the crude complex of proanthocyanidin A2 and one or more phospholipids to provide a dry complex of the proanthocyanidin A2 and one or more phospholipids.

14. The method of claim 13, further comprising grinding the dry complex of proanthocyanidin A2 and one or more phospholipids.

15. The method of claim 11, wherein the solvent is selected from the group consisting of acetate, ethyl acetate, ethanol, and mixtures thereof.

16. A composition comprising a complex of proanthocyanidin A2 and one or more phospholipids, wherein said complex is formed by:

solution; and reacting the one or more phospholipids with proanthocyanidin A2 in a solution; and concentrating the solution to provide a crude complex of proanthocyanidin A2 and one or more phospholipids.

* * * * *